US006193471B1

(12) United States Patent
Paul

(10) Patent No.: US 6,193,471 B1
(45) Date of Patent: Feb. 27, 2001

(54) PNEUMATIC CONTROL OF FORMATION AND TRANSPORT OF SMALL VOLUME LIQUID SAMPLES

(75) Inventor: Carlton H. Paul, Groton, MA (US)

(73) Assignee: PerSeptive Biosystems, Inc., Framingham, MA (US)

( * ) Notice: Subject to any disclaimer, the term of this patent is extended or adjusted under 35 U.S.C. 154(b) by 0 days.

(21) Appl. No.: 09/345,072

(22) Filed: Jun. 30, 1999

(51) Int. Cl.[7] ...................................................... F04B 19/24
(52) U.S. Cl. ............................... 417/53; 417/118; 417/121
(58) Field of Search ............................... 417/53, 118, 121

(56) References Cited

U.S. PATENT DOCUMENTS

| | | | |
|---|---|---|---|
| 3,929,411 | * 12/1975 | Takano et al. | 436/180 |
| 4,367,043 | * 1/1983 | Sweet et al. | 356/338 |
| 4,399,362 | * 8/1983 | Cormier | 250/430 |
| 4,415,011 | * 11/1983 | Grant | 141/284 |
| 5,015,591 | * 5/1991 | Meyrat et al. | 436/178 |
| 5,788,819 | * 8/1998 | Onishi et al. | 205/155 |

* cited by examiner

Primary Examiner—Teresa Walberg
Assistant Examiner—Vinod D. Patel
(74) Attorney, Agent, or Firm—Andrew T. Karnakis

(57) ABSTRACT

A process and system are provided for forming and transporting precise small volumes of liquid samples by means of controlled gas pressures. As the controlled gas pressures are changed at a multiplicity of control points in the fluid circuit, transitions take place involving the transport of small liquid samples. This transport is arrested by the geometry of the fluid circuit to produce a new state, which state remains stable until another transition is initiated by a change in the multiplicity of controlled gas pressures. Various combinations of control elements are described for effecting formation of fixed liquid volumes, transporting, mixing, and removing entrained bubbles from small liquid samples.

29 Claims, 16 Drawing Sheets

PNEUMATIC CONTROL OF FORMATION AND TRANSPORT OF SMALL VOLUME LIQUID SAMPLES

BACKGROUND OF THE INVENTION (a) Field of the Invention

This invention relates to a process, and system, and to system elements for controlling formation and movement of small volumes of liquid by means of controlled gas pressures. More particularly, this invention relates to a process and system and to system elements for gating, transporting, and mixing small volumes of liquid samples wherein the liquid samples are treated or analyzed.

(b) Description of Prior Art

Fluid circuits require gates to control fluid movement. However, at the present time, there is no accepted mechanism or process for valving fluid volumes smaller than about a hundred nanoliters. At dimensions smaller than the microliter dimension, mechanical seals are both ineffective and impractical to manufacture.

Prior to the present invention, attempts have been made to process small volumes of liquids in the nanoliter range in order to effect a chemical reaction, analysis or the like. For example, capillary microfluidic circuits have been utilized to control movement of small volumes of liquid samples by applying large voltages to the samples. The voltages induce electroosmotic flow that allows control of direction and flow rate of the liquid samples. However, there exist environmental conditions that compete with the voltage force for effecting hydrodynamic fluid flow, including those induced by small pressure gradients. Electroosmotic flow is also sensitive to variations in the ionic composition of the fluid, and on factors such as the temperature, so the control of flow rates by this method is inaccurate at best. In addition, the electroosmotic flow is sometimes detrimental to the circuit function and suppression of electroosmotic control leaves little external control. As microfluidic circuits become more complicated, electroosmotic control does not effectively provide for isolation of different parts of the circuit. As a result, the design of microfluidic circuits controlled by electroosmotic forces is limited to only simple circuit designs.

It has also been proposed to provide mechanical valves in very small fluid circuits. However, as the surface finish of most materials at micron dimensions is not uniform, devices such as mechanical valves are unreliable. In addition, the problem of aligning a mechanical valve with one or more fluid conduits is extremely difficult at micron dimensions. In another embodiment of micromachined valves, silicon diaphragms are fabricated at small dimensions to be used as valve closures, but the actuation mechanisms for these diaphragms have not been suitable for liquid transport at nanoliter scales. Thus, from a practical standpoint, mechanical valves made from these materials are not useful in systems for transporting small liquid in volumes such as that at the nanoliter level.

It has also been proposed to use nonmechanical means to control fluid movements in capillaries. The concept of utilizing menisci to control fluid movements in capillaries has been utilized extensively in devices such as in the Lang-Levy micropipette. However, prior to the present invention the use of the menisci has not been used in a capillary microfluidic system for several reasons. The most important reason has been the absence of a controllable method for creating menisci in a liquid capillary and for removing menisci from a liquid capillary. At the present time, menisci in capillaries are widely regarded as undesirable and stringent efforts are made to prevent any sources of bubbles (the most common form of menisci) including cavitation or degassing. In present liquid transport systems, bubbles become trapped at particular locations within the systems and undesirably function to obstruct liquid flow or otherwise compromise performance.

Accordingly, it would be highly desirable to provide a process and system for transporting small volumes of liquid samples such as at the nanoliter level. In addition, it would be desirable to provide such a process and system which permits the inclusion and/or the removal of menisci from a liquid sample. Furthermore, it would be desirable to provide such a process and system which permits the transport of exact small volumes of liquid sample from a storage means to a point of use in order to permit precise treatment of the sample such as for analysis or reaction. In addition, it would be desirable to provide such a process and system which permits mixture of two or more liquids. Such a process and system would permit the user to provide small samples to a point of use while providing reliable results at the point of use such as by analysis or reaction of the sample.

BRIEF DESCRIPTION OF THE INVENTION

The present invention provides a process and system for forming and transporting small volumes of liquid samples including samples having nanoliter volumes. In addition, the present invention provides a process and system for introducing menisci, arresting the movement of menisci at defined locations in the system, and for removing menisci from capillary volumes of a liquid sample. Furthermore, the present invention provides a process and system for delivering precise small volumes of liquid samples to a point of use.

The present invention is based upon the discovery that menisci can be formed, moved, arrested and removed in small capillary volumes of a liquid sample. The formation of menisci on a liquid sample permits the application of an externally controlled hydrostatic pressure on the sample without causing the sample to move within a capillary. This permits the formation of precise volumes of capillary liquid samples. The removal of menisci between two or more liquid samples permits the samples to be mixed. More generally, removal of unwanted bubbles or menisci from a capillary stream is an important part of chemical hygiene in fluid circuits, and especially in very small fluid circuits.

The active control of menisci in a capillary fluid circuit depends on the device geometry of the capillary circuit. The relationship between the device geometry and the forces in the system is an interesting problem in thermodynamics. The general capillarity equation of Young and Laplace describes the pressure difference across a meniscus necessary to keep the system in mechanical equilibrium. This equation demonstrates that the pressure difference $\Delta P$ depends on only the surface tension $\gamma$ (i.e., the surface free energy per unit area of the meniscus, with units of ergs/cm$^2$) and the shape of the meniscus.

$$\Delta P = \gamma(1/R_1 + 1/R_2) \tag{1}$$

The meniscus is a three-dimensional surface, the shape of which is described by its radii of curvature ($R_1$ and $R_2$) in two orthogonal planes. Calculation of the meniscus shape generally requires the sophisticated mathematical tools of differential geometry. However, a wetted capillary in the shape of a simple circular cylinder has a meniscus with a very simple shape as shown in FIG. 1A.

The meniscus of FIG. 1A is constrained to lie parallel to the wall of the capillary, forcing the meniscus into a hemisphere, with $R_1=R_2=$radius of the capillary. The total surface free energy of the meniscus is $2\pi r^2\gamma$. If the capillary radius is decreased incrementally by a distance dr, the surface free energy of the meniscus will decrease by $4\pi r\gamma dr$. At mechanical equilibrium, this will be balanced by a change in the pressure difference $\Delta P$ across the meniscus, where the work against the pressure difference is $\Delta P 2\pi r^2 dr$. The result is $\Delta P=2\gamma/r$, the Young-Laplace equation. If the capillary is held in a vertical orientation and dipped in a reservoir of liquid, the meniscus will rise in the capillary until mechanical equilibrium is reached where the liquid head pressure balances $\Delta P$. In this case, the capillary forces can be calculated directly from the capillary device geometry (i.e., the capillary diameter).

If the capillary channel ends abruptly, normal to a plane surface as shown in FIG. 1B, the shape of the meniscus flattens out as the meniscus approaches the opening because the meniscus surface is no longer constrained to be parallel to the capillary wall. As a result, the radius of curvature of the meniscus r' suddenly becomes infinite (a plane), and the pressure difference $\Delta P$ across the meniscus vanishes. The end of a capillary embodies a device geometry that traps a meniscus and holds it in mechanical equilibrium. The disappearance of the wetted capillary wall changes the boundary conditions that determine the shape of the meniscus, creating a barrier to movement of the meniscus and the liquid behind it.

The use of meniscus control is based upon the concept that surface free energy of a liquid can be exploited at small dimensions to control liquid motion. The actual mechanism requires that menisci be formed, moved, arrested and removed from the capillary stream under external control as a means for gating the liquid. A first element of this invention comprises a capillary gate that uses these menisci to control the movement of a liquid. A second system element of this invention for effecting formation or removal of menisci in a capillary stream is referred to herein as a "storage volume". The term "storage volume" as used herein should not be construed as requiring that the liquid actually be stored in the volume for any period of time.

In accordance with one embodiment of this invention, a system element is provided which includes a storage volume having a height of a capillary, which storage volume is in fluid communication with at least two capillary conduits. The storage volume has a width larger than the width of a capillary so that the storage volume is capable of retaining a larger volume of liquid per unit length as compared to the volume stored in a capillary of the same unit length. The storage volume also is in fluid communication with a gas having a controlled pressure thereby permitting the storage volume to function as a pressure control point on a liquid in the storage volume. A meniscus is formed within the storage volume at the interface of a liquid directed to the storage volume from an inlet capillary conduit and the gas supplied to the storage volume. The shape of this meniscus is a hemi-toroid, a mathematically simple shape having two constant radii of curvature $R_1$ and $R_2$ over its surface. The liquid is passed from the storage volume into an outlet capillary conduit The liquid in the outlet capillary conduit extends from the storage volume to a capillary gate at the end of the outlet capillary conduit, where a second meniscus is formed on the liquid surface in the outlet capillary conduit that contacts a gas in the capillary gate. The capillary gate functions as a valve. Control of liquid flow is based on the fact that the meniscus forces at the capillary gate arrest the flow of liquid in the outlet capillary conduit unless hydrostatic pressure exerted on the liquid in the outlet capillary conduit exceeds the meniscus forces.

In one embodiment, the capillary gate is a structure similar or identical to the storage volume, wherein the width of the outlet capillary conduit increases abruptly in one dimension to create a barrier to the motion of a fluid front (meniscus), thereby forming a gating point.

In a second embodiment, the capillary gate is an opening of the outlet capillary conduit on a surface, wherein the width of the outlet capillary conduit increases abruptly in two dimensions. In this embodiment, in order for the flow to continue past the gate within a capillary, a drain capillary conduit opening must be positioned on a second surface facing and very close to the outlet capillary conduit, thereby allowing a transient liquid bridge to form between the outlet capillary conduit and the drain capillary conduit.

In one application of the present invention, wherein the hydrostatic pressure in the outlet capillary conduit can be controlled to prevent or effect liquid flow, the volume of liquid in the outlet capillary conduit extending from the storage volume to the capillary gate can be dispensed in the same manner as emptying a conventional pipette. Gas pressure in the storage volume is impressed on the liquid in the outlet capillary conduit. An increase of this gas pressure causes the precise liquid volume in the outlet capillary conduit to move through the capillary gate into the drain capillary conduit. By operating in this manner, the precise liquid volume in the outlet capillary conduit from the storage volume to the capillary gate can be transferred to a point of use through the drain capillary conduit. Accuracy of the liquid volumes so dispensed is determined by the dimension of the outlet capillary conduit and not by timing of a presumed liquid flow rate. Pressure in the capillary gate can be increased after the transfer to facilitate the transport of the liquid in the drain capillary conduit to the point of use. Gas pressures in a plurality of storage volumes and capillary gates positioned in different fluid paths can be controlled simultaneously so that complex fluid flow systems can be produced. Delivery from the outlet capillary conduit, which functions as a nanopipette, is a transient event consisting of moving a defined volume of liquid from the outlet capillary conduit to the drain capillary conduit, or another point of use of the liquid.

In accordance with one embodiment of this invention, a system element is also provided for controlling the gas pressures of the plurality of gas conduits in communication with various storage volumes and capillary gates. Implementation of the control scheme of this invention requires that the gas pressures be changed at a plurality of control points, causing transitions between stable states of the microfluidic circuit that result in movement of fluid packets. The changes in pressures at these control points should be synchronized, and the magnitudes of the pressures should be both accurate and precise (preferably within 0.01 psi). The pressures can be electronically programmable both upward and downward, and it would be desirable that the response time be fast (preferably within about 20 milliseconds).

A simple electronic pneumatic controller is described which is suitable for multinode, programmable control. This controller uses proportional control feedback from a silicon pressure transducer.

DESCRIPTION OF SPECIFIC EMBODIMENTS

In the present invention, meniscus control is the basic principle that supplants mechanical valve closures at very small dimensions. The present invention is based upon the provision of system elements that are capable of forming and positioning a first meniscus on a liquid capillary stream and subsequently of forming and positioning a second meniscus on the capillary stream. The formation of a first and second meniscus permits application of pressure on the menisci which, in turn, permits the positioning of the menisci, which accomplishes the formation of precise volumes of liquid and the movement of such precise volumes of liquid to a desired position. In addition, the meniscus control permits mixing of liquids and division of samples into sub-samples when desired. These precise volumes of liquid can be formed in conduits having small cross sectional areas of capillary size where liquid movement in the conduit can be effected by capillary action. Thus, the present invention provides a process, system and system elements which permits the formation of and transportation of precise volumes of liquids through capillary paths to a point of use and permits the treatment or analysis of liquid samples in small volumes as small as nanoliter volumes.

A first system element of this invention is the capillary gate, of which five different embodiments are shown in FIGS. 2A, 2B, 2C, 2D and 2E. A capillary gate is an abrupt expansion in at least one direction in the cross-sectional dimensions of a capillary, thereby changing the shape of the meniscus as it moves through the gating point and creating a barrier to the motion of the meniscus. The pressure difference $\Delta P$ across the meniscus will decrease (as in the embodiment of FIG. 2A) or it will vanish (as in the embodiments of FIGS. 2B, 2C, and 2D). In either case, the suitable application of pneumatic and hydrostatic control pressures can fix the meniscus in mechanical equilibrium at the gating point.

Figure 1A:
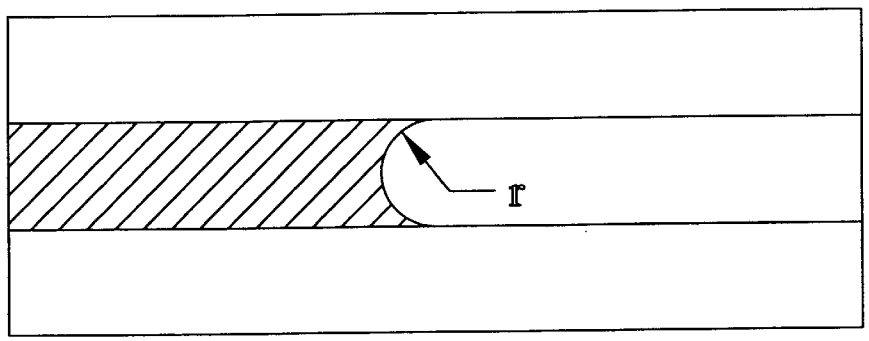
FIGS. 1A and 1B are axial section views of a meniscus in a circular cylindrical capillary.
Figure 1B:
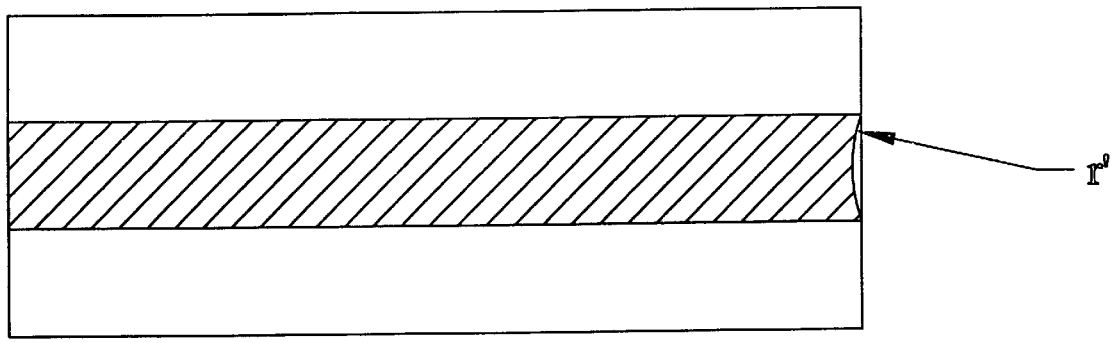
Figure 2A:
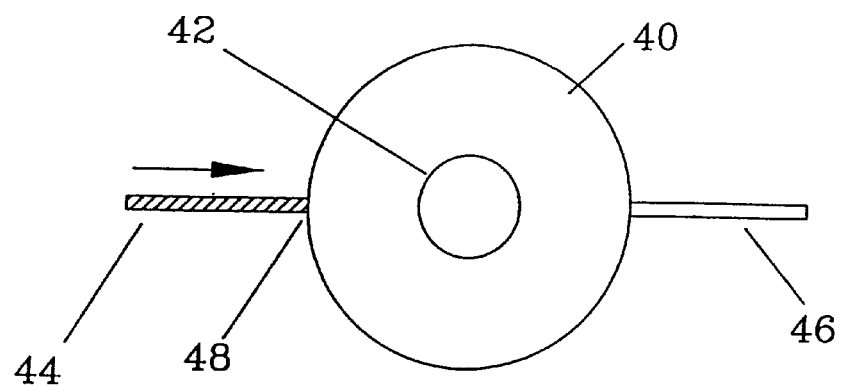
FIGS. 2A, 2B, 2C, 2D and 2E show five different embodiments of a capillary gate.

In the first embodiment of FIG. 2A, the dimensions of the capillary 44 increase along one axis (normal to the axis of the capillary) at point 48, creating a barrier to motion at that point. By arresting the motion of the meniscus, small volumes can be segregated and defined. Application of a pressure sufficient to overcome the forces holding the meniscus at the gating point permits the flow of the liquid sample to resume, allowing for the delivery of known quantities of liquid to a point of use.

Figure 2B:
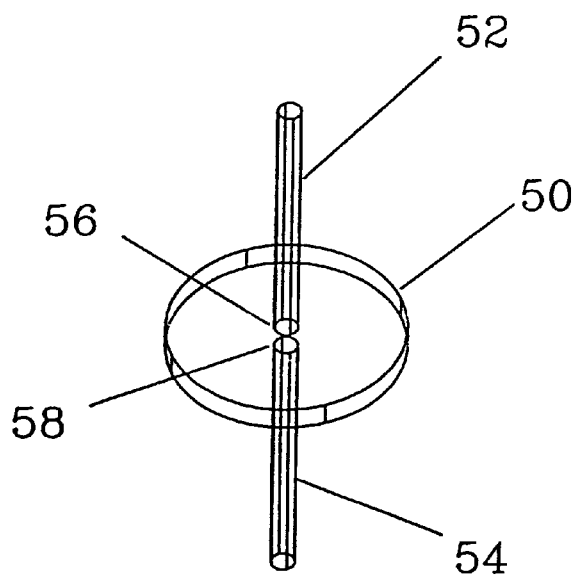

In a second embodiment of FIG. 2B, the dimensions of the inlet capillary 52 increase along two orthogonal axes (both normal to the axis of the capillary) to form a cavity 50. A short gap separates the gating point 56 from the mouth 58 of a drain capillary 54. This gap is sufficient to arrest the movement of the meniscus unless the hydrostatic pressure in the capillary 52 is great enough to extrude the liquid into the cavity. This pressure will breach the barrier at the gating point 56 by forming a liquid bridge across the gap. As indicated by the Young-Laplace equation, the barrier to motion of a meniscus across the gap in this embodiment is approximately twice as great as the barrier of FIG. 2A (with capillaries of similar dimensions).

Figure 2C:
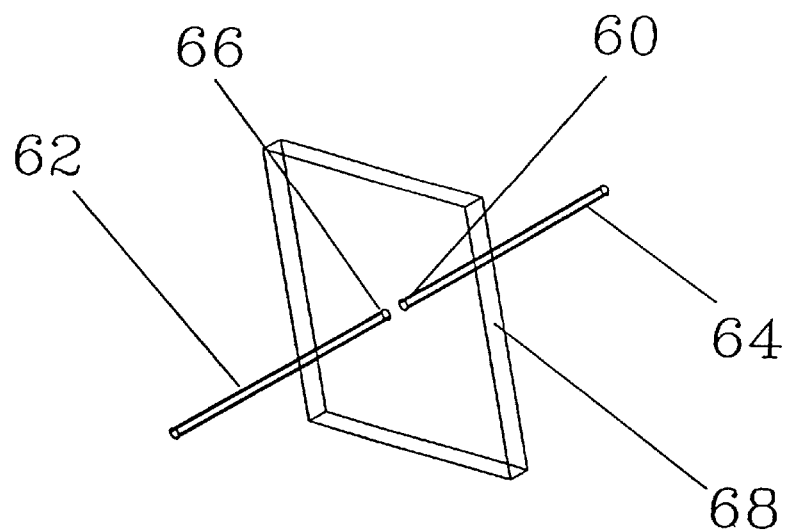

The third embodiment of FIG. 2C is a slot 68 cut at right angles through a capillary 62 and 64 to create a gap in the capillary between points 60 and 66. By creating an expansion of the capillary in two dimensions, this gap arrests meniscus movement, but allows the formation of a liquid bridge to a drain capillary 64 when the pressure applied to the volume of liquid in the meniscus is sufficient to overcome the forces maintaining the meniscus at the gate.

Figure 2D:
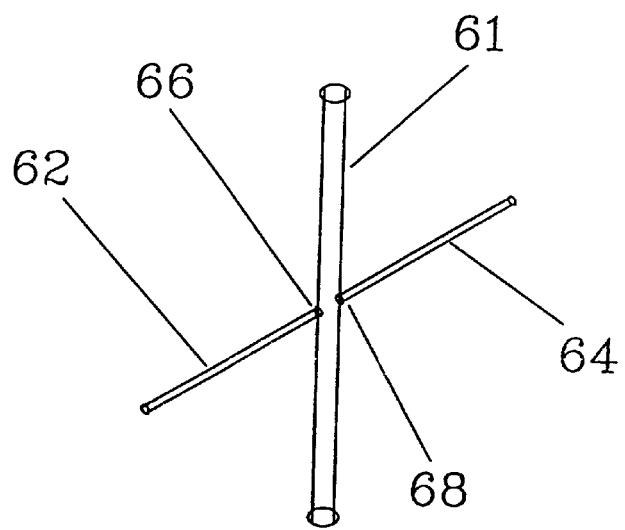

A fourth embodiment shown in FIG. 2D is formed as an intersection of a gas conduit 61 formed through a capillary 62 and 64 such as by drilling, forming a gap between points 66 and 68. This embodiment is a variant of the previous embodiment 2C.

Figure 2E:
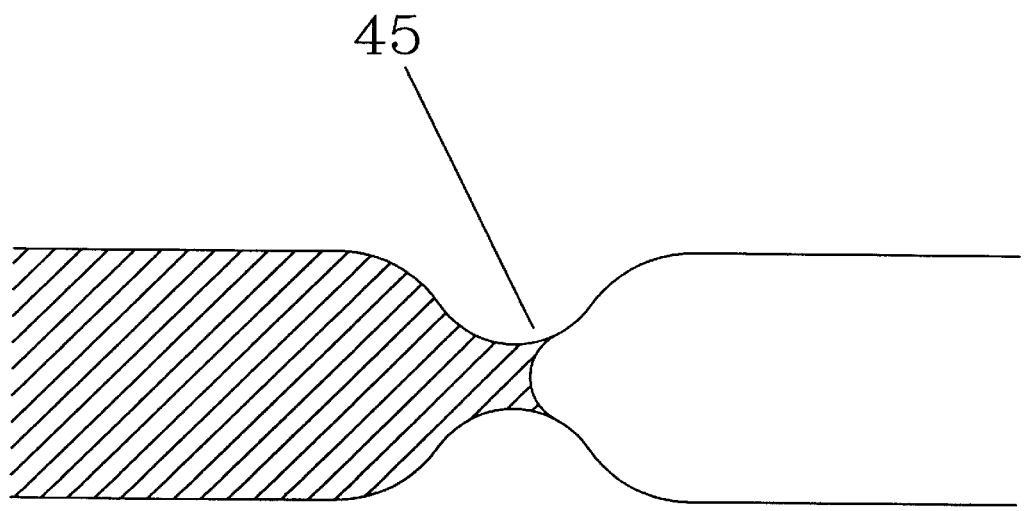

A fifth embodiment of a capillary gate, shown in FIG. 2E, does not have an expansion perpendicular to the axis of the capillary, but rather a structure similar to that of a Lang-Levy micropipette. Although the expansion is more gradual than an orthogonal wall, it still serves to arrest the motion of a meniscus by causing the meniscus to flatten out at the gating point indicated by reference numeral 45.

Figures 3A, 3B:
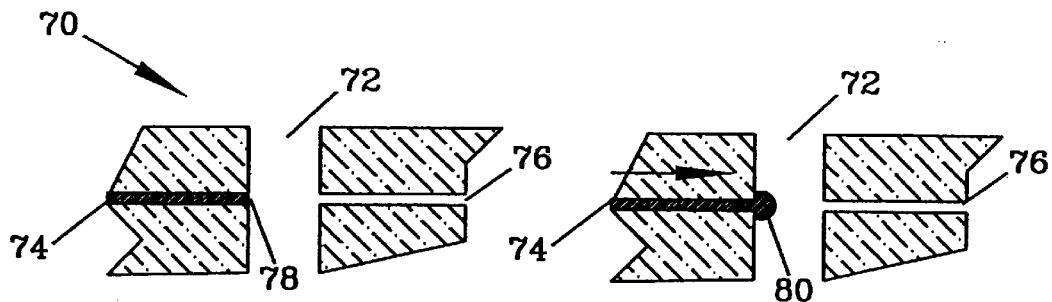
FIGS. 3A, 3B, 3C, 3D, 3E and 3F schematically depict the operation of a capillary gate in transporting liquid through a bridge from one capillary conduit to a second capillary conduit.
Figures 3C, 3D:
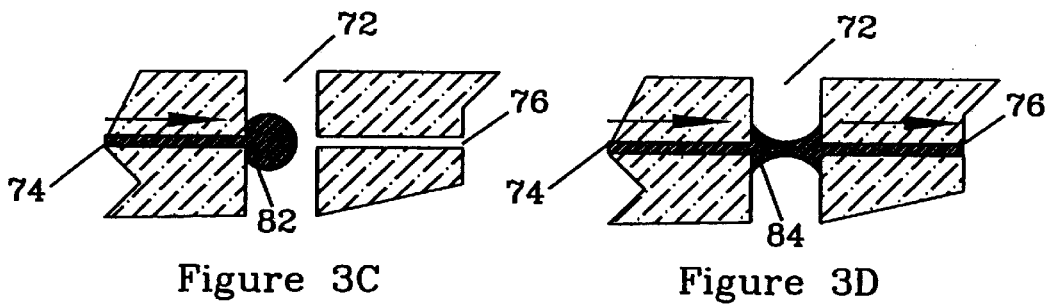
Figures 3E, 3F:
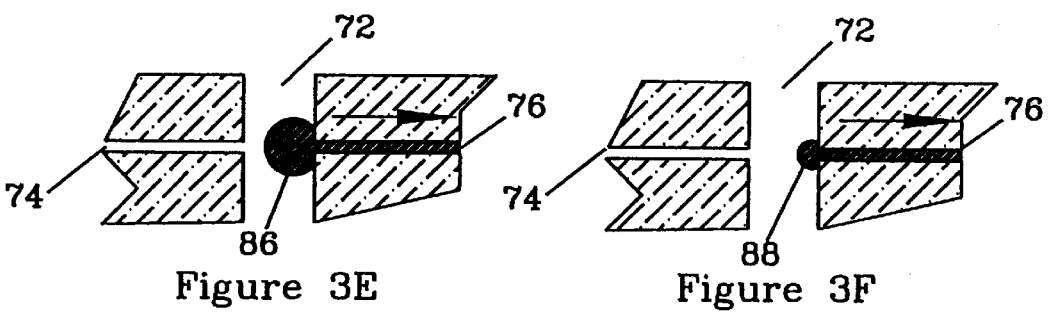

The capillary gates shown in embodiments 2B, 2C and 2D utilize gaps to create the gating point. In such embodiments, the gap creates a two-dimensional gating point, the effect of which is to require liquid to bridge the gap in order to move beyond the gate into the next capillary, or into another point of use of the liquid. As the capillary gate arrests a meniscus 78 moving along the capillary as shown in FIG. 3A, the outlet capillary conduit 74 is closed to further liquid flow. The liquid will move into the gap 72 as illustrated in FIG. 3B only when the hydraulic pressure in the capillary 74 exceeds a threshold pressure determined by the Young-Laplace equation, i.e., the meniscus free energy at the end of the outlet capillary conduit 74. When a sufficient volume of liquid is extruded into the gap 72 from outlet capillary conduit 74, it forms a liquid volume 80 that begins to bridge the distance between the opening 78 of outlet capillary conduit 74 and the opening of the drain capillary conduit 76. The liquid volume 80 increases to volume 82 (FIG. 3C), and it further increases to form a bridge 84 (FIG. 3D) between the outlet capillary conduit 74 and the drain capillary conduit 76. The drain capillary conduit 76 functions as a drain, pulling the liquid across the gap 72. The drain capillary conduit 76 consumes the bridge as illustrated in FIGS. 3E and 3F when no more liquid is available from the outlet capillary conduit 74. Bridging of the capillary gate 70 is a transient, dynamic event. However, the minimum volume sufficient to bridge the gap depends upon the dimensions of each gate design. The minimum liquid bridging volume is an important parameter because it is the lower limit on delivery volumes for this type of capillary gate. The capillary gate described above can be utilized in combination with a storage volume to produce precise volumes of liquid in the system of this invention.

Figure 4A:
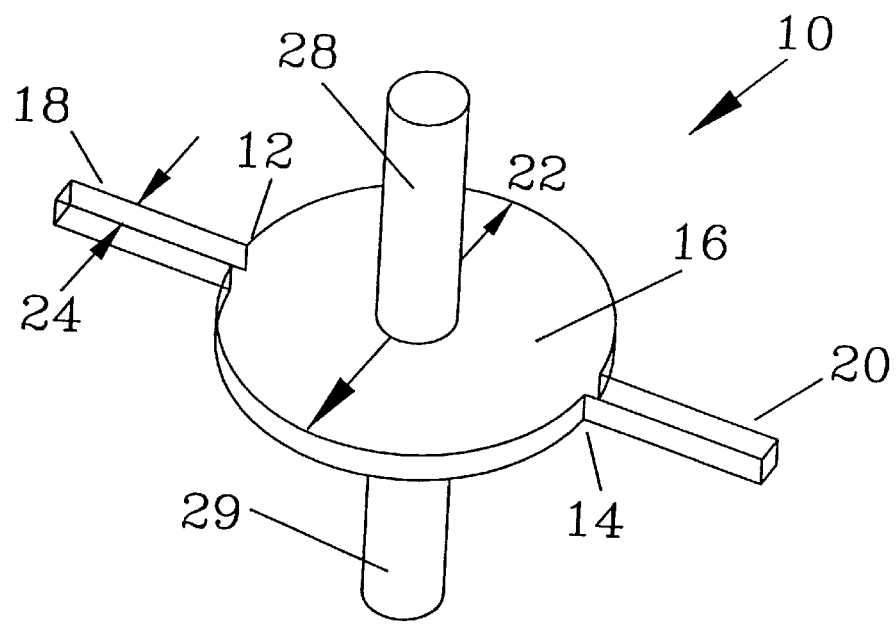
FIGS. 4A and 4B are perspective views of two embodiments of a storage volume.
Figure 4B:
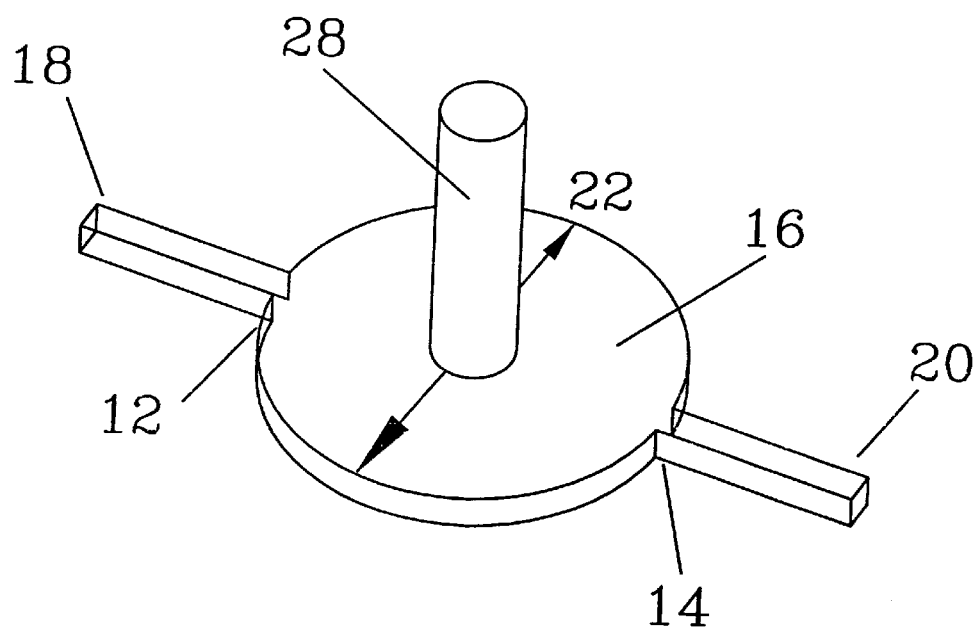
Figure 5:
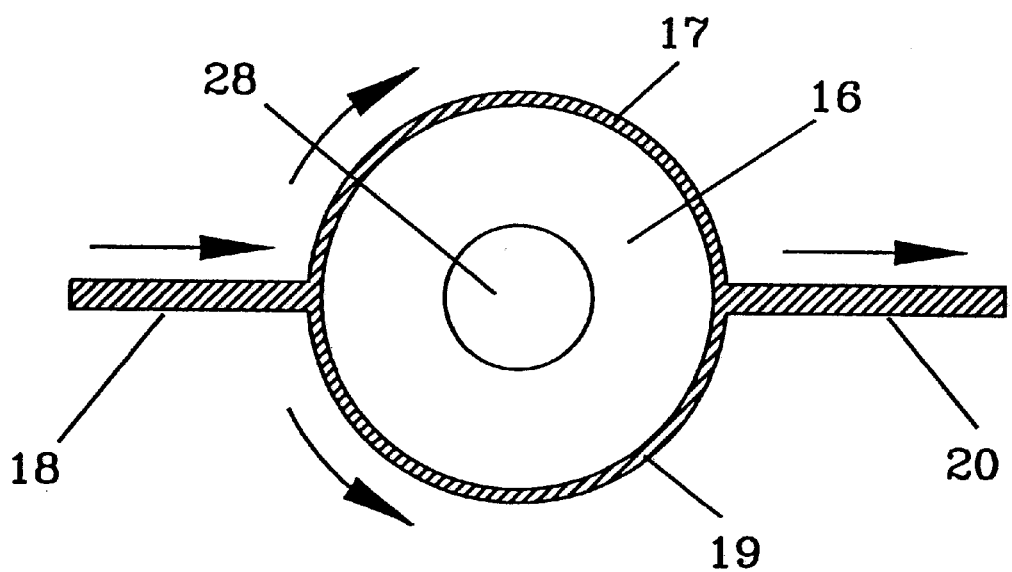
FIG. 5 is a top cross-sectional view of the storage volume of FIG. 4A.

FIGS. 4A, 4B and 5 illustrate one embodiment of the storage volume or housing of this invention for forming, gating and removing menisci in and from a capillary stream. Referring to FIGS. 4A, 4B and 5, the storage volume 16 includes an inlet capillary conduit 18, an outlet capillary conduit 20, and an interior volume 16 having a dimension substantially larger than that of a capillary conduit such as inlet capillary conduit 18 or outlet capillary conduit 20. In order to achieve the function of a capillary gate, the capillary dimension expansion created by volume 16 should be at least about two times the capillary width (or height). In one embodiment of the invention, the width of the storage volume, at its largest dimension as indicated by arrow 22, should be at least about five times as large and preferably at least about ten times as large as the width of a capillary as indicated by arrow 24. The purpose of the larger width in storage volume 16 is to cause a capillary stream of liquid entering the storage volume 16 from inlet capillary conduit 18 to be split into two sub-streams 17 and 19 which contact the perimeter 26 of the storage volume 16 when a gas is present in interior volume 16 through conduit 28 as shown in FIG. 5, thereby forming a meniscus at the liquid-gas interface. If two streams are not desired, the geometry of the storage volume could be modified, and could assume any desirable shape, such as the shape of a semi-circle for example, provided that the liquid-gas interface is formed. Conduit 28 can extend to one surface of the storage volume 16 as shown in FIG. 4B, or to both surfaces of the storage volume 16 as shown in FIG. 4A. The latter arrangement shown in FIG. 4A includes a conduit section 29.

Figure 6A:
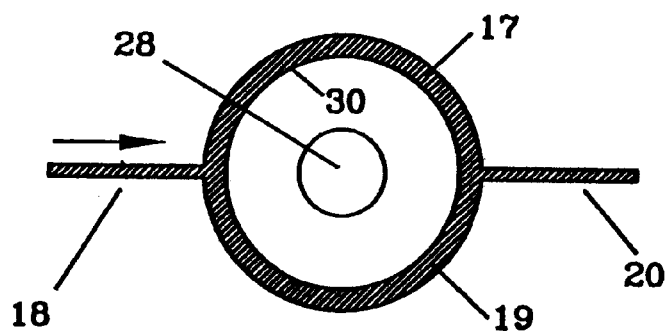
FIGS. 6A, 6B and 6C illustrate filling of a storage volume of one embodiment of this invention with a liquid.
Figure 6B:
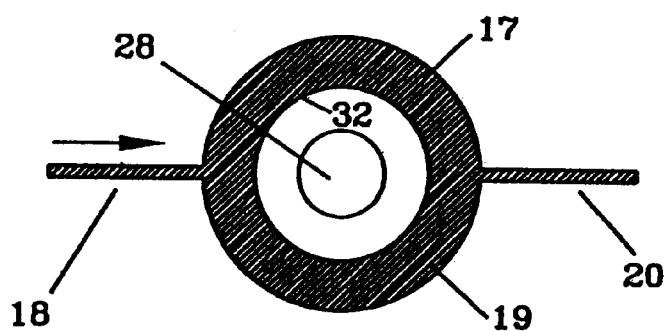
Figure 6C:
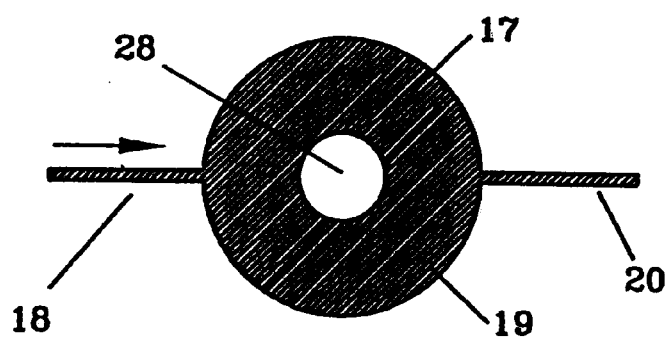

The widths of the sub-streams of 17 and 19 (e.g., the distance from the outer perimeter of the storage volume 10 to the conduit 28 that is occupied by the liquid) can be controlled by the gas pressure within storage volume 16 through gas conduit 28. As shown in FIGS. 6A, 6B and 6C, the thickness of the sub-streams 17 and 19 proceeds from the outer radius of storage volume 16 inwardly toward the gas conduit 28. As shown in FIGS. 6A and 6B, a meniscus 30 or 32 is formed as an interface between the liquid sub-streams 17 and 19 and the gas within volume 16 introduced through gas conduit 28. Referring again to FIG. 5, any bubble entering the storage volume 16 through inlet capillary conduit 18 fuses with the meniscus 30 or 32 within storage volume 16 and is removed from the liquid stream. The formation of the meniscus 30 or 32 permits the formation of precise volumes of liquid within a capillary conduit and permits the transportation of these precise volumes of liquid to a desired point of use.

Figure 7A:
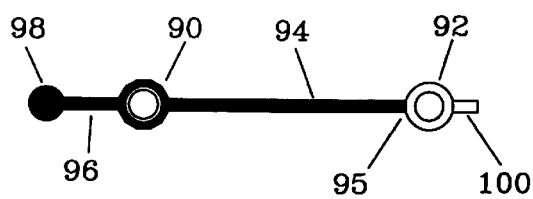
FIGS. 7A, 7B, 7C and 7D illustrate a system for the delivery of precise volumes of liquid in accordance with one embodiment of this invention.
Figure 7B:
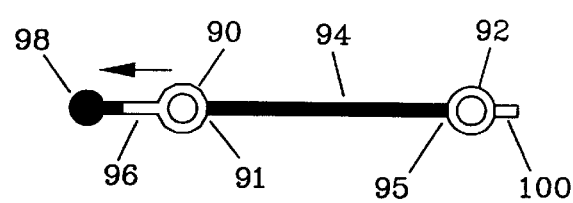

FIGS. 7A, 7B, 7C and 7D show one manner in which storage volumes and capillaries are used according to the invention to create and move a precise volume of liquid. Referring to FIG. 7A, the volume of outlet capillary conduit 94 is filled with a liquid from reservoir 98 by passing the liquid from reservoir 98, through inlet capillary conduit 96, through storage volume 90 and into outlet capillary conduit 94 to fill outlet capillary conduit 94 with liquid. By controlling the pressures in reservoir 98, the storage volume 90 and in storage volume 92, the liquid fills the outlet capillary conduit 94 up to the intersection 95 of the outlet capillary conduit 94 and storage volume 92. This intersection 95 is a capillary gate. The volume of liquid in the outlet capillary conduit 94 defines the desired precise volume of liquid to be delivered to a point of use as described hereinafter. As shown in FIG. 7B, when the pressure in storage volume 90 is increased, liquid in inlet capillary conduit 96 is directed back to reservoir 98, thereby creating a new meniscus at capillary gate 91. At the same time, the pressure difference between the pressures in volumes 90 and 92 remains below the threshold of the meniscus at the capillary gate 95 (the ΔP in the Young-Laplace equation), thereby causing the liquid in this outlet capillary conduit to remain stationary and become isolated from the reservoir 98.

Figure 7C:
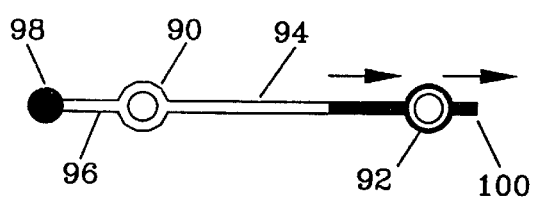
Figure 7D:
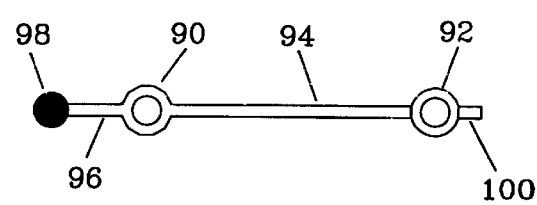
Figure 8:
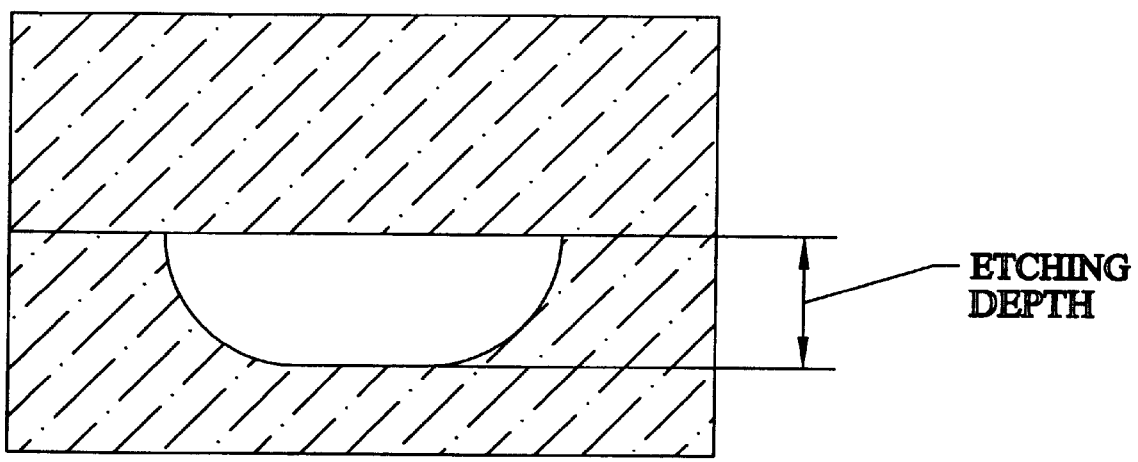
FIG. 8 is a cross section of a capillary made by isotropic etching showing the typical aspect ratio of height (etching depth) to width.

As shown in FIG. 7C, when the pressure in storage volume 90 is increased further until it exceeds the holding pressure of the capillary gate 95, liquid therein breaches the capillary gate. Transfer of all of the liquid in outlet capillary conduit 94 to drain capillary conduit 100 is then completed so that a precise volume of liquid now is isolated in drain capillary conduit 100 for delivery to a point of use as described below. When the liquid passes into the drain capillary, it can be delivered therefrom either directly or through an additional storage volume to a point of use under pressure. A capillary such as that shown in FIG. 8, made by isotropic etching to a depth of 20 micrometers, will have a ΔP of about $1 \times 10^4$ Pa (1.5 psi), and the gating threshold at a capillary gate 95 created by the same process will be roughly $5 \times 10^3$ Pa (0.75 psi).

Typical dimensions of capillaries 96, 94 and 100 are a width between about 5 micrometers and about 100 micrometers, preferably between about 20 micrometers and about 75 micrometers and a height between about 1 micrometer and about 30 micrometers, preferably between about 10 micrometers and about 20 micrometers. Typical dimensions for the storage volume 90 comprise a diameter of between about 100 micrometers and about 1000 micrometers, preferably between about 200 micrometers and about 500 micrometers and a height within the same range as the capillaries (as the capillaries and storage volumes are usually etched together). The storage volume need not have a circular cross section but can have any cross section so long that a meniscus can be formed by providing gas thereto. For example the cross sectional shape of storage volume 90 can be square, rectangular, triangular, polygonal or the like. The volume of the storage volume can be controlled by defining its major dimension so that it can store a desired volume of liquid. When the liquid within the storage volume reaches the gas conduit, the storage volume is full. Typical diameters for a capillary gate 92 are similar to those for the storage volume 90. Capillary gates shown in embodiments of FIGS. 2B, 2C, and 2D have gaps between 10 microns and 30 microns wide, the smaller gaps requiring a smaller minimum volume for forming a liquid bridge across the gap. The gas conduit need not be centrally located within the storage volume.

Figure 9:
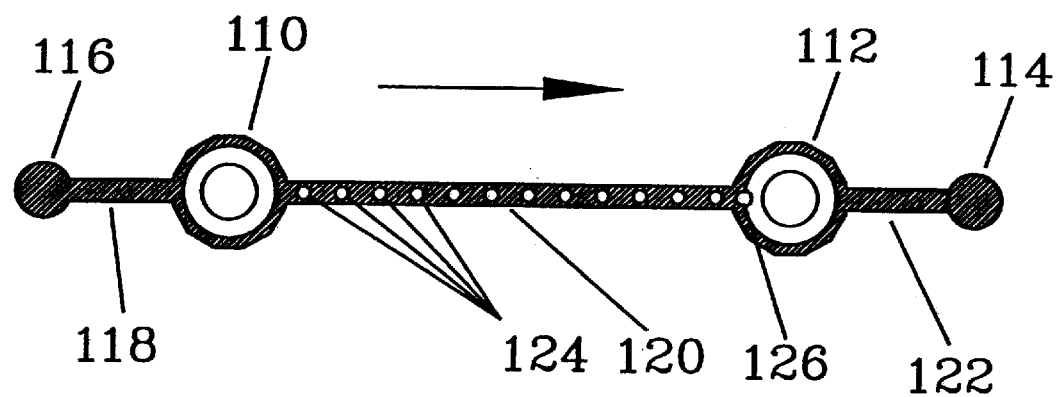
FIG. 9 illustrates the process of one embodiment of this invention for introducing and removing gas bubbles from a capillary liquid stream.

FIG. 9 shows a system element of this invention for introducing bubbles into a capillary. Liquid from reservoir 116 is passed under pressure into inlet capillary conduit 118 and thence into storage volume 110 wherein a meniscus is formed. The sample is split and then recombined for entry into outlet capillary conduit 120. A bubble 124 is introduced into the outlet capillary conduit by momentarily increasing the pressure within storage volume 110 so that the meniscus in volume 100 is moved into and along outlet capillary conduit 120. The pressures in storage volume 110 and in reservoir 116 are regulated so that liquid passes from reservoir 116, through a storage volume 110 and into the outlet capillary conduit 120. The pressure within storage volume 112 is adjusted so that bubbles 124 in outlet capillary conduit 120 are removed from the liquid by being merged with a new meniscus 57 formed in storage volume 112. The pressure in storage volume 112 also is regulated so that no bubbles are transported into capillary conduit 122. A detection means such as a refractive index detector for detecting the presence or absence of liquid samples can be installed into outlet capillary conduit 120 between storage volume 110 and storage volume 112 so that sub-samples formed from bubbles interposed therebetween can be separately analyzed or reacted as desired.

Figure 10A:
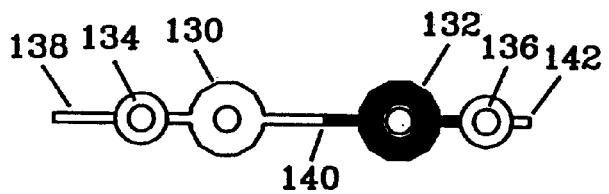
FIGS. 10A, 10B, 10C, 10D, and 10E illustrate a system for mixing liquid samples in accordance with one embodiment of this invention.
Figure 10B:
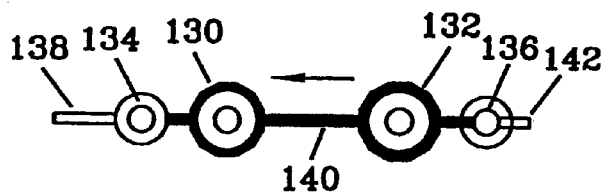
Figure 10C:
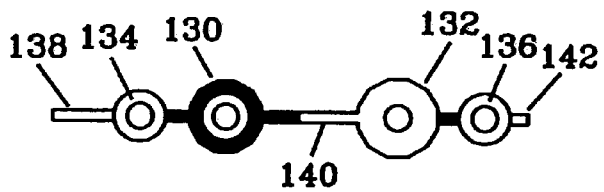

Referring to FIGS. 10A–10E, a system element of this invention is shown which can be utilized to agitate a liquid sample initially present in the storage volume 132, as might be needed if frequent or additional mixing is necessary. As shown in FIGS. 10B and 10C, the pressures within storage volumes 134 and 136 and within storage volumes 130 and 132 are controlled so that the majority of liquid is transferred from storage volume 132 into the storage volume 130 through a capillary conduit 140. This sequence is then reversed to transfer the liquid back into the storage volume 132, causing liquid shear through the capillary that effects mixing of the solution.

Figure 10D:
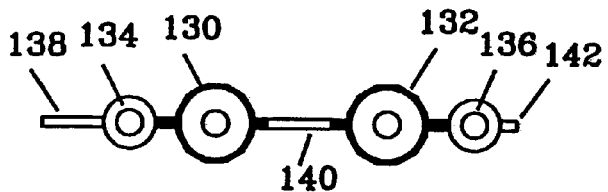
Figure 10E:
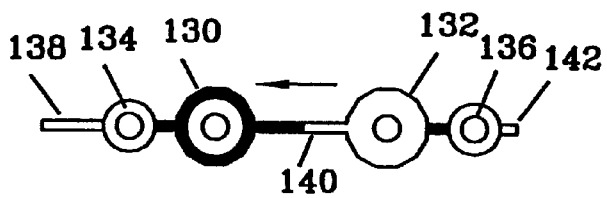

FIGS. 10D and 10E show the same system element as FIGS. 10A, 10B, and 10C, except that FIG. 10D has two unmixed liquid samples segregated by a bubble in capillary conduit 140. If the sum of the sample volumes is less than the volume of either storage volume 130 and 132, then these two separate volumes can be mixed in a manner similar to that shown in FIGS. 10A, 10B, and 10C. Such a system can be utilized, for example to react two liquids within the system of this invention.

Figure 11A:
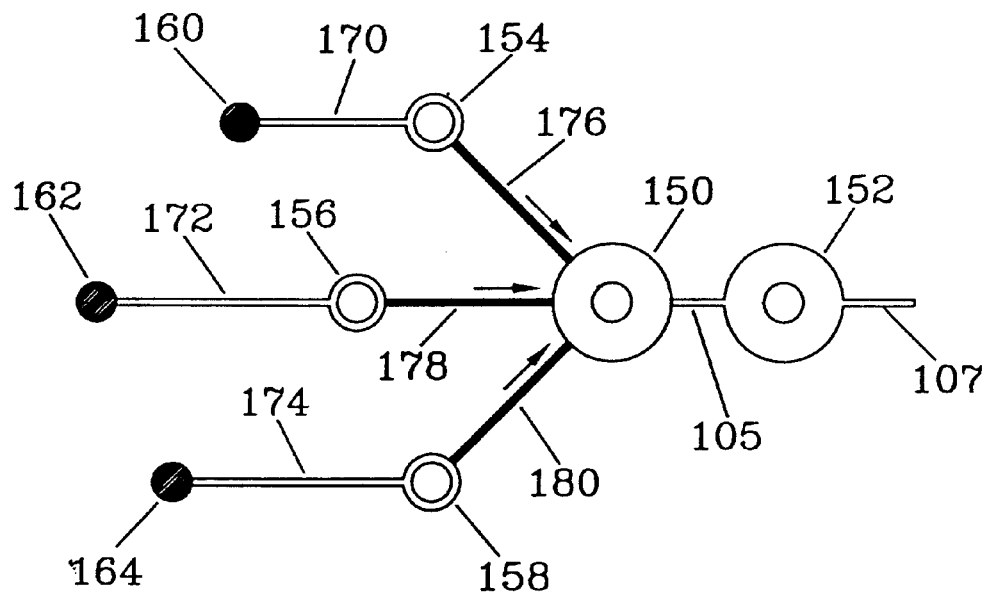
FIGS. 11A and 11B illustrate a system for combining fixed volumes of three different liquids in accordance with one embodiment of this invention.
Figure 11B:
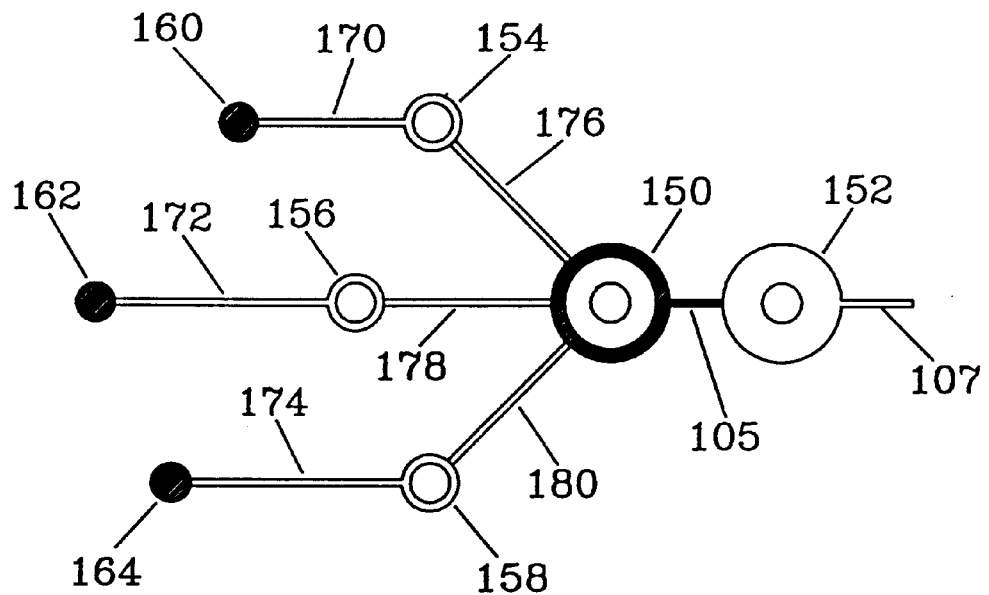

The process of using this invention for the purpose of creating precise, fixed volumes of a plurality liquid samples and of mixing these liquid samples together will be described with reference to FIGS. 11A and 11B. A supply of liquid stored in reservoir 160 which could be a first reagent for carrying out chemical synthesis is moved under pressure control to fill the capillary conduit 170, the storage volume 154, and the capillary conduit 176. Similarly, a second liquid reagent stored in reservoir 162 is moved to fill the capillary conduit 172, the storage volume 156, and the capillary conduit 178. Also, a third liquid reagent stored in reservoir 164 is moved to fill the capillary conduit 174, the storage volume 158, and the capillary conduit 180. FIG. 11A represents the state previously described for FIG. 7B, just prior to transferring the fixed volumes in capillary conduits 176, 178 and 180 through the storage volume 150 (as shown in FIG. 11B). These transfers may preferably occur simultaneously. The transfer effects mixing of the three fixed volumes of liquid transferred from capillary conduits 176, 178 and 180 to the destination storage volume 152 to produce a desired synthesis reaction. Further mixing could be accomplished by a device similar to one described in reference to FIG. 10A. Diffusion within the small dimensions shown here will also enable mixing of the three liquid volumes. The storage volume 152 can function as a point of use, or it could be in fluid communication with an analytical device such as an electrophoresis capillary or the like.

It is to be understood that the system and the process of this invention as described with reference to FIGS. 11A and 11B can be modified in accordance with the principles of this invention. For example, additional reagents can be introduced into the point of use storage volume 152 by utilizing separate conduits communicating therewith, or bubbles accidentally entrained in the capillary stream can be removed by passage through a storage volume as described with reference to FIG. 9.

Figure 12:
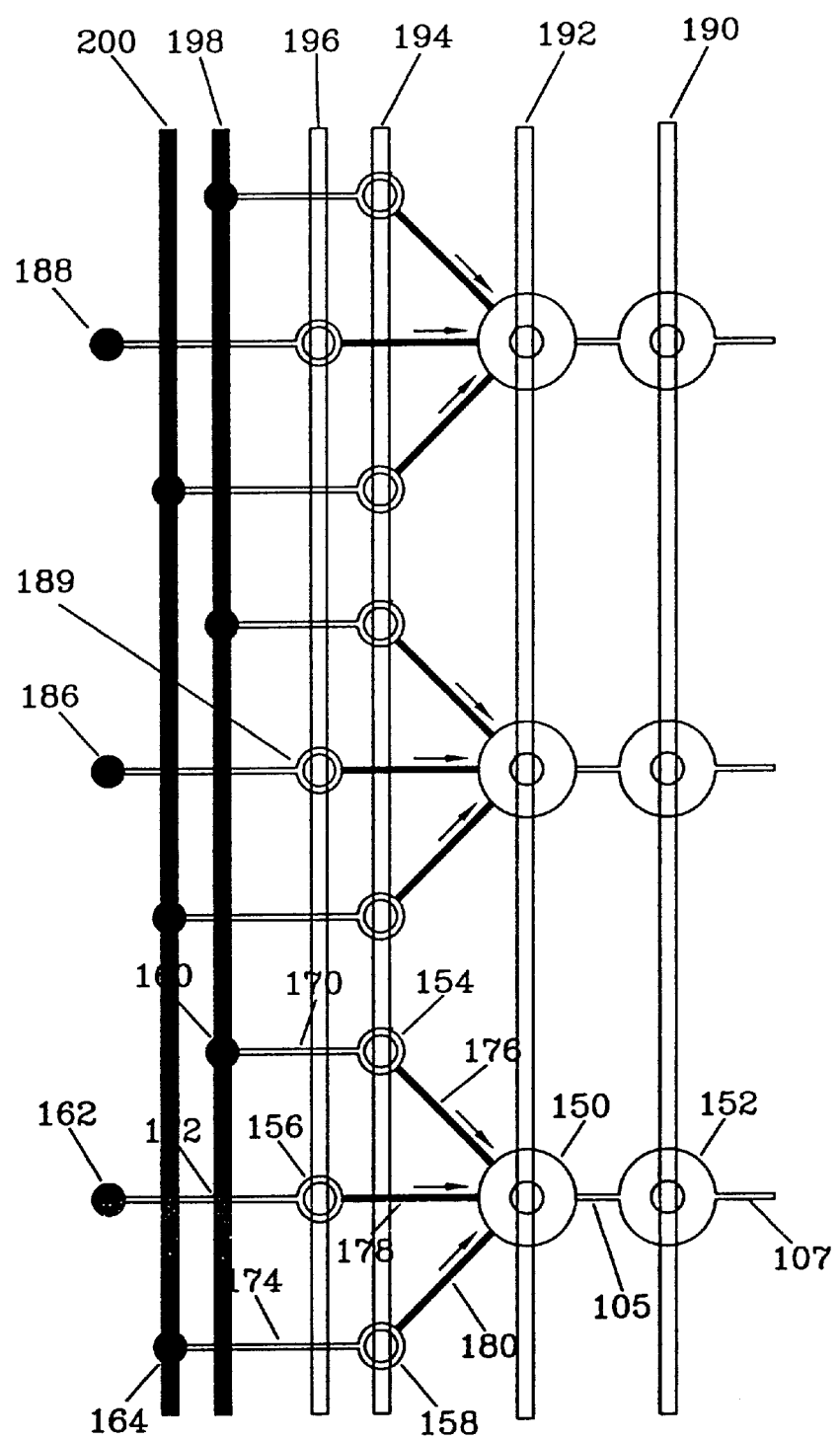
FIG. 12 illustrates a system for processing a plurality of liquid samples in a parallel fashion by means of pneumatic control through manifolds common to several similar fluid circuits in accordance with one embodiment of this invention.

The general application of using the storage volumes and capillary gates of the present invention involves setting the pressures simultaneously at a multiplicity of control points such that a transition takes place, thereby controlling the movement of a liquid from one point to another point in the fluid circuit. Such movement is arrested by the geometry of the capillary gate to produce a new stable state, and that stable state persists until the pressures at the multiplicity of control nodes are again changed to initiate a new transition to a different stable state of the fluid circuit. In addition, non-simultaneous pressures can be used to initially cause a first liquid to mix with a second, and subsequently cause a third liquid to mix with the mixed first and second liquids. Referring to FIG. 12, a plurality of subsystems identical to that device shown in FIG. 11A are arranged adjacent to each other in an array, and their corresponding gas conduits are connected together by means of the gas conduit manifolds 196, 194, 192 and 190. The three devices shown therefore can be controlled in parallel by pneumatic control elements in communication with each of the gas conduit manifolds. Two of the pipetting storage volumes of each subsystem (i.e., 156 and 189) are shown on the same control manifold, and these pipettes operate in a synchronized fashion. Manifolds 200 and 198 contain liquids which feed corresponding pipettes 164 and 160, whereas the inlet reservoirs 162, 186 and 188 are not in communication with a manifold because they receive different liquid samples from one subsystem to the next. Aside from the liquid sample manifolds 200 and 198, the subsystems shown in FIG. 12 are isolated and independent from each other. This arrangement of subsystems is particularly suited for multiplex operation and is useful in high throughput screening of potential candidates in drug discovery processes.

Figure 13:
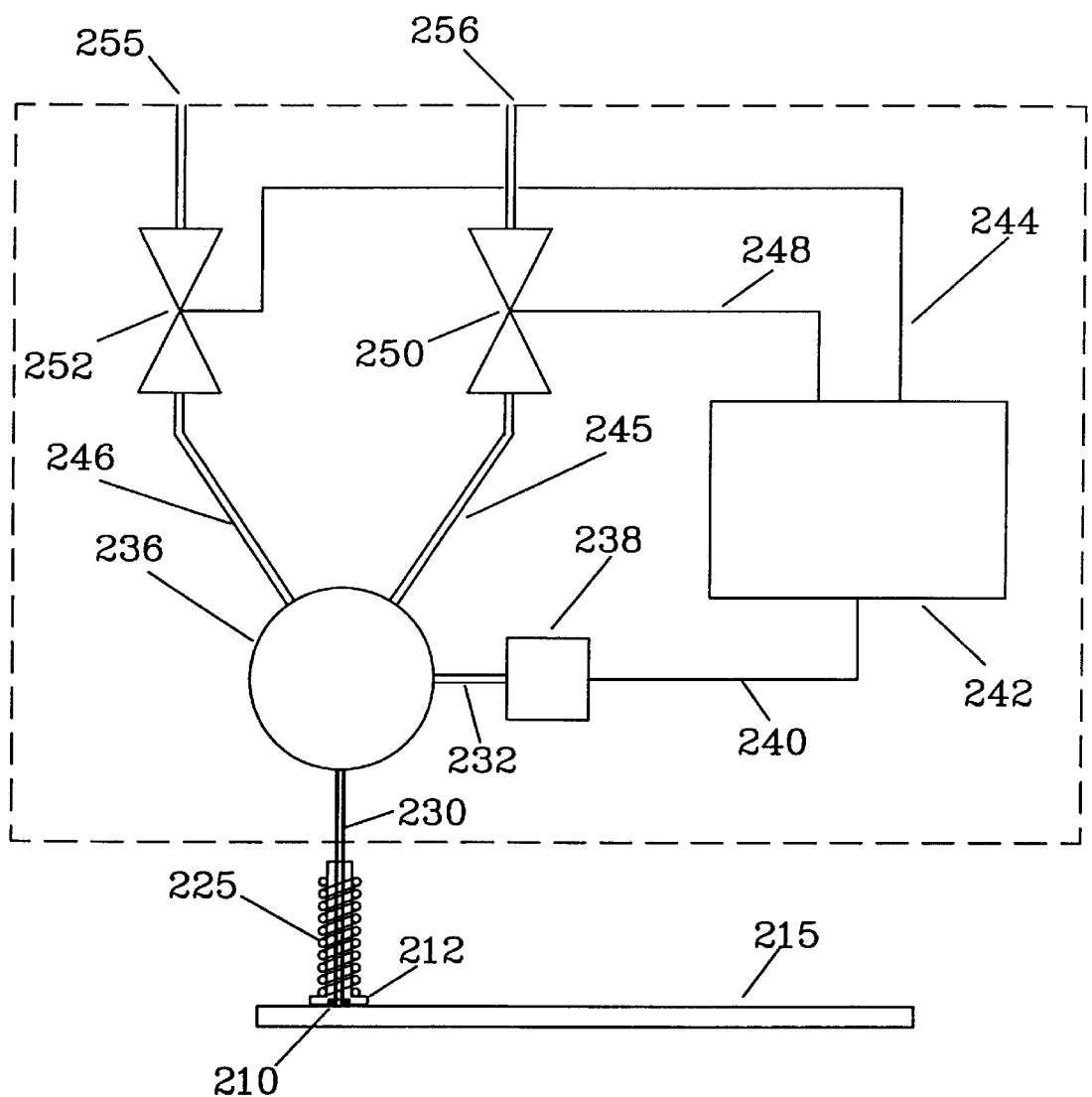
FIG. 13 shows a mechanical schematic diagram of a pneumatic controller element in accordance with one embodiment of this invention operating on one node contained in a microfluidic circuit.

FIG. 13 shows a mechanical schematic diagram of a gas pressure control element used to communicate with one of the gas conduit manifolds of FIG. 12. A microfluidic circuit 215 has an opening (not shown) on its surface communicating with one of the gas manifolds. A conduit 230 forms a spring loaded face-seal with this opening by means of the O-ring 210, the ferrule 212, and the compression spring 225, and conduit 230 is in communication with an accumulator 236 wherein the pressure is measured by a pressure transducer 238. An electronic feedback loop consisting of the pressure transducer 238, a control circuit 242, a pressurizing valve 250 and a relieving valve 252, all joined by signal leads 240, 248 and 244, establishes whether the pressurizing valve 250 is open or closed, and whether the relieving valve 252 is open or closed, thereby changing the pressure in the accumulator 236 as needed. The pressurizing valve 250 is in communication with a source of elevated pressure 256, whereas the relieving valve 252 is in communication with a source 255 of lower pressure or with a vacuum.

Figure 14:
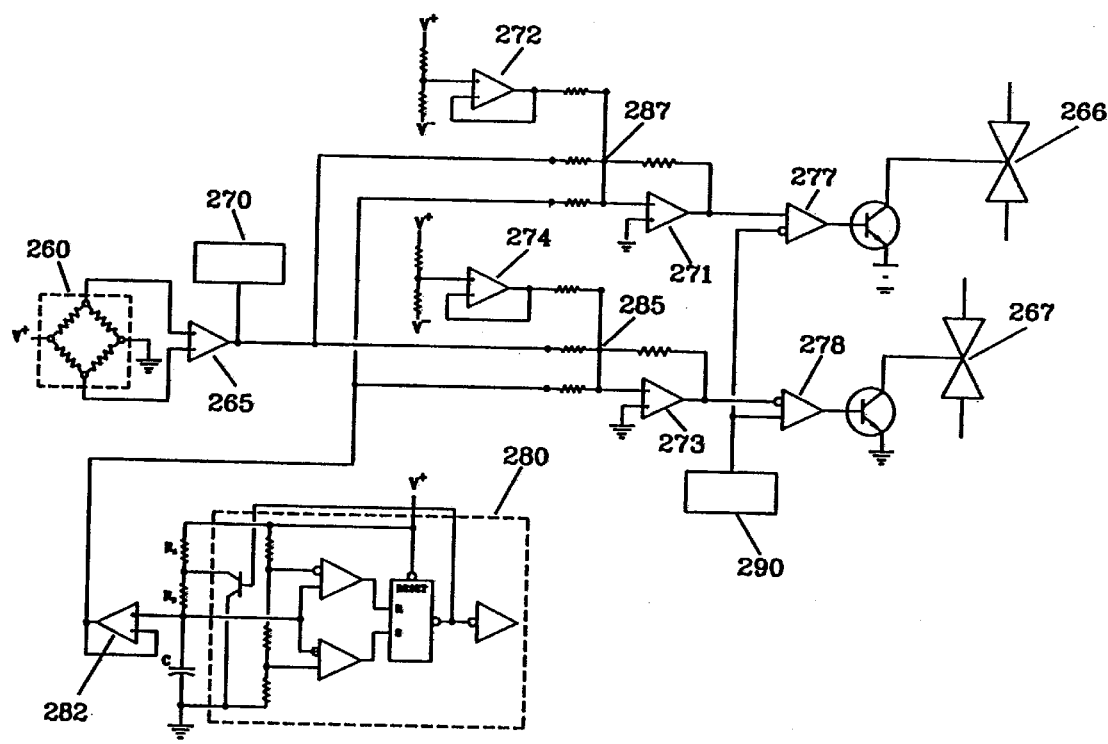
FIG. 14 shows an electronic schematic diagram for the pneumatic controller element of FIG. 13, suitable for regulating the pressure at a single node of the microfluidic circuit.

FIG. 14 shows an electronic schematic diagram of the control circuit 242, one element of the feedback loop shown in FIG. 13. The signal from the pressure transducer 260 is amplified by an instrumentation amplifier 265, and is routed to the summing points 285 and 287 of two operational amplifiers 271 and 273. Also routed to the summing points 287 and 285 of amplifiers 271 and 273 are corresponding offset voltages from the voltage followers 272 and 274, as well as a sawtooth signal made by the astable multivibrator 280. The signals emanating from the amplifiers 271 and 273 are therefore sawtooth waveforms that rise and fall with respect to the baseline as the pressure in transducer 260 falls and rises. These signals are compared to a setpoint voltage from a variable voltage source 290, which may be a digital-to-analog converter (DAC) in communication with a computer, by the voltage comparators 277 and 278. The voltage comparators cause the pressurizing valve 266 or the relieving valve 267 to open and close at the same frequency as the sawtooth signal, but for longer or shorter periods, or not at all, depending on the relation of the sawtooth waveform to the setpoint voltage from voltage source 290.

This type of circuit is known in the art as a proportional controller. Within a pressure range known as the proportioning band, the duty cycle of the valve controlling the gas pressure is proportional to the error in the pressure. As the gas pressure approaches the desired setpoint, the intervals during which the valve is open become shorter and shorter. The duty cycle of the valve becomes zero as the desired pressure is achieved. This allows a response time as fast as the valve can open or close, without overshooting the desired setpoint pressure. The signal from the pressure transducer 260 can be amplified to assure that the pneumatic controller will respond to very small changes in pressure, with a preferred precision in the regulated gas pressure of ±0.01 psi. The pressure may be recorded or monitored by a device 270, which may be an analog-to-digital converter in communication with a computer. The setpoint voltages from the voltage source 290 under the direction from a computer can be calibrated to correspond to specific pressures. The offset voltages from voltage followers 272 and 274 are chosen such that the pressurizing valve and the relieving valve are never actuated at the same time.

The prior art in electronic regulation of gas pressure teaches several methods, of which the preferred is a proportional-integral-derivative (PID) response to an error in the pressure. The PID method is typically embodied in an algorithm executed by a microprocessor, with the intention of achieving a high level of stability at one fixed pressure under varying loads. The pneumatic controller of the present invention achieves a somewhat different end by making an inexpensive hardware proportional controller with the objective of changing the pressure frequently and accurately at a multiplicity of control nodes. The pressure changes are synchronized at the multiplicity of control nodes and a multiplicity of desired setpoint pressures can be obtained at each of the multiplicity of control nodes. In this manner, the formation and effective transport of precise liquid volumes within a complex microfluidic circuit can be accomplished with negligible impact on the gas pressure control.

The systems and system elements of this invention have been described with respect to microfluidic circuits or devices. Such devices can take a variety of forms, but they are generally characterized as planar structures having a plurality of ports for introducing or withdrawing liquids to and from the device, one or more reservoirs for storing liquid samples or liquid reagents, and a plurality of capillary scale channels for transporting and/or mixing liquids, conducting chemical analyses, separating components of a mixture or the like. In this context, the microfluidic devices as well as the system and system elements of this invention can be formed by conventional photolithography and etching techniques or by molding plastic compositions which are well known in the art. Representative suitable substrates from which the system and system elements of this invention can be formed include glass, quartz, silicon, polycarbonate, polymethylmethacrylate or the like. However, the wetting characteristics of these different substrates must be taken into account for proper design of the fluid circuits.

What is claimed is:

1. A system for delivering a liquid sample to a point of use which comprises:

a storage volume in fluid communication with a gas, an inlet capillary conduit for receiving a liquid sample in fluid communication with said storage volume, an outlet capillary conduit for receiving a liquid sample in fluid communication with said storage volume, a drain capillary conduit, said storage volume being dimensioned to form a meniscus on a capillary liquid stream passing within said storage volume, said outlet capillary conduit being in fluid communication with said storage volume, a capillary gate in fluid communication with said drain capillary conduit, and in fluid communication with a gas, and being dimensioned to permit liquid to flow through said capillary gate between said outlet capillary conduit and said drain capillary conduit, a means for controlling gas pressure in said storage volume, and a means for controlling pressure in said inlet capillary conduit.

2. A system element of a system for delivering a liquid sample to a point of use which comprises:

a storage volume in fluid communication with a gas, an inlet capillary conduit in fluid communication with said storage volume, an outlet capillary conduit in fluid communication with said storage volume, and said storage volume being dimensioned to form a meniscus on a capillary liquid stream passing through said storage volume.

3. A system element of a system for delivering a liquid sample to a point of use which comprises:

a capillary gate being in fluid communication with a gas, an inlet capillary conduit being in fluid communication with said capillary gate, a drain capillary conduit-being in fluid communication with said capillary gate, said capillary gate comprising an open space being dimensioned to permit liquid to flow through a gas and between said inlet capillary conduit and said drain capillary conduit by forming a liquid bridge between said outlet capillary conduit and said drain capillary conduit.

4. A system for forming and delivering a precise volume of a liquid to a point of use which comprises:

a storage volume in fluid communication with a gas, an inlet capillary conduit in fluid communication with said storage volume, an outlet capillary conduit in fluid communication with said storage volume, said storage volume being dimensioned to form a meniscus on a capillary liquid stream passing within said storage volume, a capillary gate being in fluid communication with a gas, being in fluid communication with said outlet capillary conduit and being in fluid communication with said drain capillary conduit, said capillary gate comprising an open space being dimensioned to permit liquid to flow through a gas and between said outlet capillary conduit and said drain capillary conduit by forming a liquid bridge between said outlet capillary conduit and said drain capillary conduit, and means for controlling gas pressure in said storage volume and in said capillary gate to fill said outlet capillary conduit with said liquid.

5. A system element for mixing liquids in a system for delivering a liquid sample to a point of use which comprises:

a first storage volume in fluid communication with a gas, a first inlet capillary conduit for a first liquid in fluid communication with said first storage volume, an outlet capillary conduit in fluid communication with said first storage volume, said first storage volume being dimensioned to form a meniscus on a capillary liquid stream passing within said volume, a second storage volume in fluid communication with a gas, a second inlet capillary conduit for a second liquid in fluid communication with said second storage volume, said outlet capillary conduit being in fluid communication with said second storage volume, said second storage volume being dimensioned to form a meniscus on a capillary liquid stream passing within said volume, a means for controlling gas pressure in said first storage volume, and means for controlling gas pressure in said second storage volume to effect mixing of said first liquid with said second liquid.

6. A system element for mixing a plurality of liquids in a system for delivering a liquid sample to a point of use which comprises:

a plurality of liquid paths in fluid communication with a common capillary gate, each of said liquid paths comprising a reservoir for a liquid, an inlet capillary conduit in fluid communication with a storage volume, said storage volume being in fluid communication with a gas conduit, and an outlet capillary conduit being in fluid communication with said storage volume, said storage volume being dimensioned to form a meniscus on a capillary liquid stream passing within said storage volume, said capillary gate being in fluid communication with a gas conduit, being in fluid communication with each of said outlet capillary conduits and being in communication with at least one drain capillary conduit, said capillary gate comprising an open space being dimensioned to permit liquid to flow through a gas and between each of said outlet capillary conduits and said at least one drain capillary conduit by forming a liquid bridge between each of said outlet capillary conduits and said at least one drain capillary conduit.

7. A system for mixing and delivering a plurality of liquids to a plurality of points of use comprising a plurality of the system elements of claim 6, wherein a conduit for a gas in each of said system elements is in fluid communication with common gas conduit manifolds and whereby the plurality of system elements are controlled together and in a synchronous manner.

8. The system as in any of claims 1–6, in which said storage volume has a perimeter which is generally circular.

9. The system of claim 8, further including a conduit in fluid communication with said storage volume at a location spaced from said inlet and said outlet capillary conduits, and about centrally of said circular perimeter, for accomplishing the fluid communication of said storage volume with a gas.

10. The system as in any of claims 1–6, in which said inlet capillary conduit has a width, and in which said storage volume has a width at least about twice as large as the width of said inlet capillary conduit.

11. The system as in any of claims 1–6, in which said inlet capillary conduit has a height, and in which said storage volume has a height about the same as that of said inlet capillary conduit.

12. The system as in any of claims 1–6, in which said outlet capillary conduit has a width, and in which said storage volume has a width at least about twice as large as the width of said outlet capillary conduit.

13. The system as in any of claims 1–6, in which said outlet capillary conduit has a height, and in which said storage volume has a height about the same as that of said outlet capillary conduit.

14. The system as in any of claims 1–6, in which said capillary gate comprises an abrupt expansion of said capillary conduit in at least one dimension.

15. The system as in any of claims 1–6, in which said capillary gate comprises an abrupt expansion of said capillary conduit in two dimensions.

16. A gas pressure control element which comprises:

a gas accumulator in fluid communication with at least one first conduit for a gas in fluid communication with the storage volume or with the capillary gate of the system of claim 1, a pressure transducer in fluid communication with said accumulator;

a first valve in fluid communication with said gas accumulator, said first valve also in fluid communication with a first reservoir of gas at an elevated pressure;

a second valve in fluid communication with said gas accumulator, said second valve also in fluid communication with a second reservoir of gas at a pressure lower than the pressure of the first reservoir, or under vacuum;

and said pressure transducer in electrical communication with an electrical circuit controlling opening and closing of said first valve and said second valve.

17. The process for delivering a liquid sample through an inlet capillary conduit, a storage volume, an outlet capillary conduit, a capillary gate, and a drain capillary conduit to a point of use, which comprises:

delivering a liquid sample through an inlet capillary conduit to a storage volume, said storage volume being in fluid communication with a gas, being dimensioned to form a meniscus on a capillary liquid stream passing within said volume, said outlet capillary conduit being in fluid communication with said storage volume and being in fluid communication with a capillary gate, retaining said liquid sample in said outlet capillary conduit, said capillary gate being in fluid communication with a drain capillary conduit and being in fluid communication with a gas and being dimensioned to permit fluid to flow through a gas and between said outlet capillary conduit and said drain capillary conduit, passing said liquid sample from said outlet capillary conduit through said capillary gate to said drain capillary conduit, and delivering said liquid sample from said drain capillary conduit to said point of use.

18. The process for forming a precise volume of a liquid sample using an inlet capillary conduit, a storage volume, and an outlet capillary conduit, which comprises:

delivering a liquid sample through an inlet capillary conduit to a storage volume, forming a meniscus on said liquid sample in said storage volume, passing said liquid sample from said storage volume to an outlet capillary conduit having a fixed volume to fill said outlet capillary conduit, and retaining said liquid sample in said outlet capillary conduit.

19. The process for mixing two liquids with a system element in a system for delivering a liquid sample to a point of use, each system element including an inlet capillary conduit and a storage volume, which comprises:

delivering a first liquid through a first inlet capillary conduit to a first storage volume, said storage volume being in fluid communication with a gas and being dimensioned to form a meniscus on a capillary liquid, delivering a second liquid through a second inlet capillary conduit to a second storage volume, said second storage volume being in fluid communication with a gas, being dimensioned to form a meniscus on a capillary liquid stream, and controlling pressure in said first storage volume and in said second storage volume to effect passage of said first liquid and of said second liquid within said outlet capillary conduit connecting said first storage volume and said second storage volume.

20. The process for mixing a plurality of liquid samples in a system for delivering a liquid sample to a point of use, the system including a plurality of liquid paths, each of said liquid paths in fluid communication with a common capillary gate and comprising a reservoir for a liquid, an inlet capillary conduit in fluid communication with a storage volume and said reservoir, said storage volume being in fluid communication with a gas, and an outlet capillary conduit in fluid communication with said storage volume, said storage volume being dimensioned to form a meniscus on a capillary liquid stream, the system further including at least one drain capillary conduit, the process comprising:

introducing a liquid into each of the plurality of liquid paths, passing each of said liquids through said capillary gate, said capillary gate being in fluid communication with a gas, with each of said outlet capillary conduits and with said at least one drain capillary conduit, and said capillary gate comprising an open space being dimensioned to permit liquid to flow through a gas and between each of said outlet capillary conduits and said at least one drain capillary conduit by forming a liquid bridge between each of said outlet capillary conduits and said at least one drain capillary conduit.

21. Apparatus for transporting a liquid sample through a capillary, comprising:

a housing having a volume and an inlet and an outlet spaced from said inlet;

a first capillary path in communication with said storage volume through said inlet, said first capillary path defining a first axis parallel to the direction of flow of liquid in said first capillary path, said storage volume being dimensioned at said inlet so as to expand in at least one direction at an angle greater than zero relative to said first axis;

a second capillary path in communication with said storage volume through said outlet; said second capillary path defining a second axis parallel to the direction of flow of liquid in said second capillary path, said storage volume being dimensioned at said outlet so as to expand in at least one direction at an angle greater than zero relative to said second axis.

22. The apparatus of claim 21, wherein said storage volume is dimensioned at said inlet so as to expand in a plurality of directions at an angle greater than zero relative to said first axis.

23. The apparatus of claim 21 or 22, wherein said storage volume is dimensioned at said outlet so as to expand in a plurality of directions at an angle greater than zero relative to said second axis.

24. The apparatus of claim 21, wherein said storage volume is in communication with a gas effective to form a meniscus at the interface of said gas and liquid in said storage volume.

25. The apparatus of claim 21, further comprising means for controlling the pressure in said first capillary path.

26. The apparatus of claim 21 or 25, further comprising means for controlling pressure in said storage volume.

27. The apparatus of claim 25, wherein said liquid sample occupies said first capillary path and comprises a meniscus, and wherein said pressure is controlled in order to arrest the movement of said meniscus at the expansion of said inlet, or to cause movement of said meniscus past the expansion of said inlet.

28. The apparatus of claim 21, wherein said expansion at said inlet is defined by a gap between said first capillary path and said storage volume.

29. A process for transporting a sample volume from a first fluid path having a first fluid path dimension and an axis parallel to the direction of fluid flow to a second fluid path, whereby an interface is defined between said first fluid path and said second fluid path such that said interface has an interface dimension at an angle greater than zero relative to said axis that is greater than said first fluid path dimension, said sample volume having a meniscus at its leading edge, said meniscus having a meniscus pressure, said process comprising:

applying pressure to said sample volume in said first fluid path, said pressure being sufficient to overcome said meniscus pressure and cause said sample volume to cross said interface and enter said second fluid path.

* * * * *